United States Patent
Ishihara et al.

(10) Patent No.: US 8,524,956 B2
(45) Date of Patent: Sep. 3, 2013

(54) METHOD OF PURIFYING (Z)-1-CHLORO-3,3,3-TRIFLUOROPROPENE

(75) Inventors: Akira Ishihara, Saitama (JP); Yasuo Hibino, Saitama (JP); Ryoichi Tamai, Saitama (JP)

(73) Assignee: Central Glass Company, Limited, Ube-shi (JP)

( * ) Notice: Subject to any disclaimer, the term of this patent is extended or adjusted under 35 U.S.C. 154(b) by 253 days.

(21) Appl. No.: 13/142,531

(22) PCT Filed: Jan. 25, 2010

(86) PCT No.: PCT/JP2010/050879
§ 371 (c)(1),
(2), (4) Date: Jun. 28, 2011

(87) PCT Pub. No.: WO2010/090086
PCT Pub. Date: Aug. 12, 2010

(65) Prior Publication Data
US 2011/0270001 A1    Nov. 3, 2011

(30) Foreign Application Priority Data

Feb. 3, 2009 (JP) .................... 2009-022704
Jan. 21, 2010 (JP) .................... 2010-010601

(51) Int. Cl.
*C07C 17/38* (2006.01)

(52) U.S. Cl.
USPC .......................................... 570/178; 570/177

(58) Field of Classification Search
None
See application file for complete search history.

(56) References Cited

U.S. PATENT DOCUMENTS

| | | |
|---|---|---|
| 5,087,329 A | 2/1992 | Felix |
| 6,013,846 A | 1/2000 | Wismer et al. |
| 6,018,084 A | 1/2000 | Nakada et al. |
| 6,077,982 A | 6/2000 | Yates et al. |
| 6,120,652 A * | 9/2000 | Hibino et al. .................... 203/51 |
| 6,179,967 B1 * | 1/2001 | Nishimura et al. ............. 203/60 |
| 6,235,951 B1 | 5/2001 | Sakyu et al. |
| 6,844,475 B1 | 1/2005 | Tung et al. |
| 2005/0020862 A1 | 1/2005 | Tung et al. |

FOREIGN PATENT DOCUMENTS

| | | |
|---|---|---|
| EP | 0 729 932 A1 | 9/1996 |
| GB | 2 329 386 A | 3/1999 |
| JP | 7-133240 A | 5/1995 |
| JP | 9-12487 A | 1/1997 |
| JP | 9-183740 A | 7/1997 |
| JP | 10-72381 A | 3/1998 |
| JP | 10-310541 A | 11/1998 |
| JP | 11-158089 A | 6/1999 |
| JP | 11-180908 A | 7/1999 |
| JP | 11-209316 A | 8/1999 |
| JP | 11-279088 A | 10/1999 |
| JP | 2000-508315 A | 7/2000 |
| WO | WO 2005/012212 A2 | 2/2005 |
| WO | WO 2005/014512 A2 | 2/2005 |

OTHER PUBLICATIONS

International Search Report dated Feb. 16, 2010 (two (2) pages).

* cited by examiner

*Primary Examiner* — Sudhakar Katakam
(74) *Attorney, Agent, or Firm* — Crowell & Moring LLP

(57) ABSTRACT

Disclosed is a method of purifying (Z)-1-chloro-3,3,3-trifluoropropene of the formula [1], comprising: distilling a mixture containing (Z)-1-chloro-3,3,3-trifluoropropene and 1-chloro-1,3,3,3-tetrafluoropropane ($CF_3CH_2CHClF$), wherein the distilling is performed by extractive distillation of the mixture in the coexistence of at least one kind of compound selected from the group consisting of halogenated hydrocarbons of the formula [2], halogenated unsaturated hydrocarbons, nitriles, ketones, carbonates, ethers, esters and alcohols as an extractant

[Chem. 8]

$$CF_nCl_{3-n}CHXCClF_mH_{2-m} \quad [2]$$

where X represents a hydrogen atom (H), a fluorine atom (F) or a chlorine atom (Cl); n represents an integer of 0 to 3; and m represents an integer of 0 to 2.

8 Claims, No Drawings

METHOD OF PURIFYING (Z)-1-CHLORO-3,3,3-TRIFLUOROPROPENE

TECHNICAL FIELD

The present invention relates to a method of purifying 1-chloro-3,3,3-trifluoropropene, which is useful as a functional material such as a cleaning agent, a solvent, a coolant or a propellant and as an intermediate for various functional products. More particularly, the present invention relates to a purification method for separating (Z)-1-chloro-3,3,3-trifluoropropene from a crude product of 1-chloro-3,3,3-trifluoropropene containing 1-chloro-1,3,3,3-tetrafluoropropane.

BACKGROUND ART 1,1-Dichloro-1-fluoroethane (HCFC-141b) and dichloropentafluoropropane (HCFC-225) are hydrofluorocarbons that are currently used as solvents, cleaning agents or the like but are subjected to regulation in view of the fact that each of 1,1-dichloro-1-fluoroethane and dichloropentafluoropropane causes a large effect on the global environment because of high ozone depletion potential (ODP). In the field of use of these hydrofluorocarbons, there has been a demand for alternative materials that do not exert an effect or exert a very small effect on the global environment.

On the other hand, 1-chloro-3,3,3-trifluoropropene is a fluorine-containing unsaturated hydrocarbon that has a double bond in its molecule and shows very low ODP and global warming potential (GWP). Attention is being thus given to the 1-chloro-3,3,3-trifluoropropene as one alternative material. Patent Document 1 discloses, as a first step for the production of 1,1,1,3,3-pentafluoropropane, a process of producing 1-chloro-3,3,3-trifluoropropene by reaction of 1,1,1,3,3-pentachloropropane with hydrogen fluoride in a gas phase. Patent Document 2 discloses a process of producing 1,1,1-trifluoro-3-chloro-2-propene (1-chloro-3,3,3-trifluoropropene) by reaction of 1,1,1,3,3-pentachloropropane with hydrogen fluoride in the absence of a catalyst as a first step for the production of 1,1,1,3,3-pentafluoropropane. Further, Patent Document 3 discloses a process of producing 1-chloro-3,3,3-trifluoropropene by reacting 1,1,1,3,3-pentachloropropane in a liquid phase at a temperature lower than 150° C. in the presence of either a Lewis acid catalyst or a mixture thereof in a reaction vessel, continuously extracting hydrogen chloride and 1-chloro-3,3,3-trifluoropropene generated in the reaction vessel and isolating 1-chloro-3,3,3-trifluoropropene The above processes however have a problem that the selectivity of the target product becomes deteriorated due to the occurrence of many by-products.

In general, distillation is adopted in industrial production process to separate a liquid or a liquefiable gas mixture. In the case where, at the time of separation of the target product containing any by-product as impurity, the boiling point of the target compound is very close to the boiling point of the by-product compound, it is very difficult to efficiently separate the target compound from the impurity by distillation.

Extractive distillation is thus adopted as one effective distillation method. Herein, "extractive distillation" refers to a method of separating a mixture of at least two kinds of components after adding a third component of high boiling point as an extractant to the mixture and thereby changing the relative volatility of the components to be separated. For example, Patent Document 4 discloses that pentafluoroethane and chloropentafluoroethane can be separated favorably by extractive distillation with the use of 1,2-dichlorotetrafluoroethane as an extractant. Patent Document 5 discloses a process of separating pentafluoroethane and chloropentafluoroethane by extractive distillation with the use of a ketone such as acetone or n-pentane or a paraffin as an extractant. Further, Patent Document 6 discloses a process of separating pentafluoroethane and 1,1,1-trifluoroethane by extractive distillation with the use of a $C_1$-$C_2$ chlorocarbon or chlorohydrocarbon as an extractant.

As a technique relevant to the present invention, Patent Document 7 discloses a process of separating 1,1,1,3,3-pentafluoropropane from a mixture thereof with 1-chloro-3,3,3-trifluoro-trans-1-propene by distillation, wherein the distillation is performed in the coexistence of, as a third component, a saturated hydrocarbon compound having a higher boiling point than 1-chloro-3,3,3-trifluoro-trans-1-propene.

PRIOR ART DOCUMENTS

Patent Documents

Patent Document 1: Japanese Laid-Open Patent Publication No. 9-183740
Patent Document 2: Japanese Laid-Open Patent Publication No. 11-180908
Patent Document 3: International Publication No. 2005-014512
Patent Document 4: U.S. Pat. No. 5,087,329
Patent Document 5: Japanese Laid-Open Patent Publication No. 7-133240
Patent Document 6: Japanese Laid-Open Patent Publication No. 9-12487
Patent Document 7: Japanese Laid-Open Patent Publication No. 11-209316

DISCLOSURE OF THE INVENTION

As mentioned above, 1-chloro-3,3,3-trifluoropropene is obtained in the form of a mixture of trans and cis isomers by fluorination of 1,1,1,3,3-pentachloropropane.

[Chem. 1]

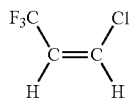  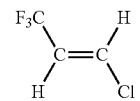

Cis (Z) isomer
normal boiling point:
39.0° C.

Trans (E) isomer
normal boiling point:
21.0° C.

As the normal boiling point of cis-1-chloro-3,3,3-trifluoropropene and the normal boiling point of trans-1-chloro-3,3,3-trifluoropropene are 39.0° C. and 21.0° C., respectively, cis-1-chloro-3,3,3-trifluoropropene can be easily separated from trans-1-chloro-3,3,3-trifluoropropene by atmospheric distillation.

When 1-chloro-1,3,3,3-tetrafluoropropane (HCFC-244fa, boiling point: 42.2° C.) coexists as an impurity component with 1-chloro-3,3,3-trifluoropropene, however, it is difficult to separate 1-chloro-3,3,3-trifluoropropene from 1-chloro-1,3,3,3-tetrafluoropropane by ordinary distillation operation due to the fact that the boiling point of cis-1-chloro-3,3,3-trifluoropropene is very close to the boiling point of 1-chloro-1,3,3,3-tetrafluoropropane. By ordinary distillation operation, 1-chloro-3,3,3-trifluoropropene is distilled along with, rather than separated from, 1-chloro-1,3,3,3-tetrafluoropropane (cis isomer, Z form).

In this way, there is a problem that (Z)-1-chloro-3,3,3-trifluoropropene and 1-chloro-1,3,3,3-tetrafluoropropane cannot be easily separated from each other by ordinary distillation operation.

For the industrial application of extractive distillation, the selection of an extractant is a very important requirement. It is further necessary to optimize the distillation conditions for such a specific extractant. There is a need to develop new extractive distillation operation since extractive distillation operations using conventional extractants cannot be applied as they are to the separation of the material of the present invention.

In view of the above problems, the present inventors have made extensive researches on the suitable technique to enhance the separation of 1-chloro-3,3,3-trifluoropropene from 1-chloro-1,3,3,3-tetrafluoropropane for industrial-scale production of (Z)-1-chloro-3,3,3-trifluoropropene and have found that it is possible to separate (Z)-1-chloro-3,3,3-trifluoropropene very easily by distillation in the presence of a specific extractant. The present invention is based on this finding.

Namely, the present invention includes the following aspects [1] to [8].

[1] A method of purifying (Z)-1-chloro-3,3,3-trifluoropropene of the formula [1], comprising: distilling a mixture containing (Z)-1-chloro-3,3,3-trifluoropropene of the formula [1] and 1-chloro-1,3,3,3-tetrafluoropropane (CF$_3$CH$_2$CHClF),

[Chem. 2]

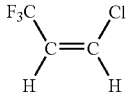

[1]

wherein the distilling is performed by extractive distillation of the mixture in the coexistence of at least one kind of compound selected from the group consisting of halogenated hydrocarbons of the formula [2], halogenated unsaturated hydrocarbons, nitriles, ketones, carbonates, ethers, esters and alcohols as an extractant

[Chem. 3]

 [2]

where X represents a hydrogen atom (H), a fluorine atom (F) or a chlorine atom (Cl); n represents an integer of 0 to 3; and m represents an integer of 0 to 2.

[2] The method according to aspect 1, wherein the halogenated hydrocarbons are at least one selected from the group consisting of 1,1-dichloro-3,3,3-trifluoropropane, 1,1,3-trichloro-3,3-difluoropropane, 1,1,1,3,3-pentachloropropane and 1,1,2-trichloro-3,3,3-trifluoropropane.

[3] The method according to aspect 1, wherein the halogenated unsaturated hydrocarbons are at least one selected from the group consisting of 1,2-dichloro-3,3,3-trifluoropropene, 1,2,3-trichloro-3,3-difluoropropene, 1,2,3-tetrachloro-3-fluoropropene, 1,3-dichloro-3,3-difluoropropene, 2,3-dichloro-3,3-difluoropropene, 1,3-dichloro-3-fluoropropene and 2,3,3-trichloro-3-fluoropropene.

[4] A method of purifying (Z)-1-chloro-3,3,3-trifluoropropene of the formula [1], comprising: distilling a mixture containing (Z)-1-chloro-3,3,3-trifluoropropene of the formula [1] and 1-chloro-1,3,3,3-tetrafluoropropane (CF$_3$CH$_2$CHClF),

[Chem. 4]

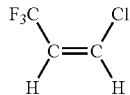

[1]

wherein the distilling is performed by extractive distillation of the mixture in the coexistence of at least one compound selected from the group consisting of 1,1-dichloro-3,3,3-trifluoropropane, 1,1,3-trichloro-3,3-difluoropropane, 1,1,1,3,3-pentachloropropane, 1,1,2-trichloro-3,3,3-trifluoropropane, acetone, acetonitrile, dimethyl carbonate, ethanol, 1,3-dioxolane and γ-butyrolactone as an extractant.

[5] The method according to any one of aspects 1 to 4, wherein the extractant has a normal boiling point of 50 to 220° C.

[6] The method according to any one of aspects 1 to 5, wherein the extractant contains less than 50 mass % of water.

[7] The method according to any one of aspects 1 to 5, wherein the amount of the extractant is 10 to 10000 parts by weight per 100 parts by mass of the mixture containing the 1-chloro-3,3,3-trifluoropropene of the formula [1] and the 1-chloro-1,3,3,3-tetrafluoropropane.

[8] The method according to any one of claims 1 to 6, further comprising:

distilling a mixture obtained after the extractive distillation and containing the extractant and either the 1-chloro-1,3,3,3-tetrafluoropropane or (Z)-1-chloro-3,3,3-trifluoropropene extracted with the extractant, thereby separating the extractant and the 1-chloro-1,3,3,3-tetrafluoropropane or (Z)-1-chloro-3,3,3-trifluoropropene from the mixture;

returning the separated 1-chloro-1,3,3,3-tetrafluoropropane or (Z)-1-chloro-3,3,3-trifluoropropene to the reaction system; and recovering and reusing the separated extractant.

The present invention is directed to the separation a mixture containing an unsaturated compound in contrast to the separation of a mixture containing a saturated compound in Patent Documents 4-6. As one invention using a starting material containing an unsaturated compound, Published Japanese translation of PCT application No. 2000-508315 discloses a process for obtaining 1,1,1,3,3-pentafluoropropane with high purity by reacting a mixture of 1,1,1,3,3-pentafluoropropane and 1-chloro-3,3,3-trifluoropropene under specific reaction conditions and removing 1-chloro-3,3,3-trifluoropropene from the mixture. Although this process is very useful, it is extremely difficult to separate the target compound, 1,1,1,3,3-pentafluoropropane, by ordinary distillation operation (as is discussed in the above document).

The relative volatility of a mixture of compounds varies depending on the molecular structures and physical properties such as polarity of the compounds. Although the behavior of the mixture during distillation is estimated to change largely due to the variation in relative volatility, it is generally extremely difficult to separate to the mixture of the compounds of close boiling points. For example, the separation of (Z)-1-chloro-3,3,3-trifluoropropene and 1-chloro-1,3,3,3-tetrafluoropropane is very difficult through the use of no extractant as in the after-mentioned comparative example.

It has thus been unknown whether the fluorine-containing unsaturated compound, (Z)-1-chloro-3,3,3-trifluoropropene, can be distilled efficiently from the starting material of the present invention.

However, the present inventors have made an industrially advantageous finding that it is possible to easily distill (Z)-1-chloro-3,3,3-trifluoropropene by extractive distillation of the mixture containing (Z)-1-chloro-3,3,3-trifluoropropene and 1-chloro-1,3,3,3-tetrafluoropropane with the use of an extractant that changes the relative volatility of the mixture to within a specific range.

There is no other known technique to distill (Z)-1-chloro-3,3,3-trifluoropropene selectively and efficiently from the mixture of (Z)-1-chloro-3,3,3-trifluoropropene and 1-chloro-1,3,3,3-tetrafluoropropane.

The present inventors have further found that it is feasible to distillate a mixture containing the extractant and either the 1-chloro-1,3,3,3-tetrafluoropropane or (Z)-1-chloro-3,3,3-trifluoropropene extracted with the extractant, thereby separating the extractant and the 1-chloro-1,3,3,3-tetrafluoropropane or (Z)-1-chloro-3,3,3-trifluoropropene from the mixture, return the separated 1-chloro-1,3,3,3-tetrafluoropropane or (Z)-1-chloro-3,3,3-trifluoropropene to the reaction system and recover and reuse the separated extractant.

As described above, the method of the present invention enables easy purification of the fluorine-containing unsaturated hydrocarbon, (Z)-1-chloro-3,3,3-trifluoropropene, by distillation of the mixture thereof containing the very close boiling point impurity component. The method of the present invention also allows reuse of the extractant for significant reduction in waste. Accordingly, the method of the present invention is superior for industrial production.

DETAILED DESCRIPTION

The present invention has the effect that (Z)-1-chloro-3,3,3-trifluoropropene can be separated at high purity on industrial scale by extractive distillation of a mixture of (Z)-1-chloro-3,3,3-trifluoropropene and 1-chloro-1,3,3,3-tetrafluoropropane with the use of a specific extractant The method of the present invention will be described in detail below. In general, the composition of the mixture containing (Z)-1-chloro-3,3,3-trifluoropropene and 1-chloro-1,3,3,3-tetrafluoropropane to which the method of the present invention is applied varies depending on the reaction conditions and distillation purification conditions in the production of 1-chloro-3,3,3-trifluoropropene. Although the reaction product has a specific composition depending on various parameters such as the reaction temperature and pressure and hydrogen chloride concentration for chemical equilibrium in the reaction system and the purification distillation conditions, the composition of the reaction product is generally controlled in such a manner as to attain a maximum production efficiency or a minimum production cost in the production of 1-chloro-3,3,3-trifluoropropene.

There is no particular limitation on the composition of the mixture to be subjected to separation in the method of the present invention. The mole ratio of (Z)-1-chloro-3,3,3-trifluoropropene and 1-chloro-1,3,3,3-tetrafluoropropane is generally set in such a manner that the amount of 1-chloro-1,3,3,3-tetrafluoropropane is in the range of 0.001 to 1 mol per 1 mol of (Z)-1-chloro-3,3,3-trifluoropropene. There is no technical problem even if the amount of 1-chloro-1,3,3,3-tetrafluoropropane exceeds 1 mol. However, the use of such a large amount of 1-chloro-1,3,3,3-tetrafluoropropane leads to increases in the circulation rate of 1-chloro-1,3,3,3-tetrafluoropropane and in the economical load. It is thus preferable to control the amount of 1-chloro-1,3,3,3-tetrafluoropropane to within the above range.

There is also no particular limitation on the process of preparation of the mixture containing (Z)-1-chloro-3,3,3-trifluoropropene and 1-chloro-1,3,3,3-tetrafluoropropane to which the method of the present invention is applied. It is feasible to use the mixture prepared by e.g. fluorinating a halogenated hydrocarbon with hydrogen fluoride, more specifically fluorinating 1,1,1,3,3-pentachloropropane with hydrogen fluoride in the absence of a catalyst in a liquid phase under high-temperature and high-pressure conditions to thereby obtain 1-chloro-3,3,3-trifluoropropene, or fluorinating 1,1,1,3,3-pentachloropropane with hydrogen fluoride in the presence of a fluorinated alumina or chromia catalyst in a gas phase. In general, only a slight amount of 1-chloro-1,3,3,3-tetrafluoropropane is generated in the above process but is concentrated together with (Z)-1-chloro-3,3,3-trifluoropropene by repeated cycles of distillation separation of (E)-1-chloro-3,3,3-trifluoropropene.

By the above process, 1-chloro-3,3,3-trifluoropropene is produced as a mixture of a trans isomer (E isomer) and a cis isomer (Z isomer). The isomer mixture of 1-chloro-3,3,3-trifluoropropene can be subjected as it is to the method of the present invention. It is however particularly preferable to subject the isomer mixture to the method of the present invention after removing the trans isomer, (E)-1-chloro-3,3,3-trifluoropropene, from the mixture by distillation, in order to obtain the target compound, (Z)-1-chloro-3,3,3-trifluoropropene, efficiently with high purity.

The distillation separation of (Z)-1-chloro-3,3,3-trifluoropropene and 1-chloro-1,3,3,3-tetrafluoropropane can be achieved by increasing or decreasing the relative volatility of these components to be higher than or lower than 1.

The relative volatility is defined as the ratio of equilibrium factors of constituent components of a fluid mixture. In the case of the fluid mixture containing (Z)-1-chloro-3,3,3-trifluoropropene (A) and 1-chloro-1,3,3,3-tetrafluoropropane (B) as the constituent components, the relative volatility is given by the following formula. Relative volatility (A/B)= (gas-phase molar fraction/liquid-phase molar fraction)$_A$/ (gas-phase molar fraction/liquid-phase molar fraction)$_B$ In the method of the present invention, the extractant is used to change the relative volatility of 1-chloro-1,3,3,3-tetrafluoropropane to (Z)-1-chloro-3,3,3-trifluoropropene.

In the case of flowing (Z)-1-chloro-3,3,3-trifluoropropene out of the reaction system, it is favorable to use the extractant that is capable of changing the relative volatility to be higher than 1, more preferably 2 or higher. When the relative volatility is higher than 1, the amount of (Z)-1-chloro-3,3,3-trifluoropropene in the gas phase increases with the gas-phase molar fraction of (Z)-1-chloro-3,3,3-trifluoropropene so that (Z)-1-chloro-3,3,3-trifluoropropene can be separated by distillation.

In the case of flowing 1-chloro-1,3,3,3-tetrafluoropropane out of the reaction system, there may also be used the extractant that is capable of changing the relative volatility to be lower than 1. In this case, the amount of (Z)-1-chloro-3,3,3-trifluoropropene in the liquid phase increases with the liquid-phase molar fraction of (Z)-1-chloro-3,3,3-trifluoropropene so that 1-chloro-1,3,3,3-tetrafluoropropane can be distilled.

When the relative volatility is 1, the respective phases become the same in composition whereby it impossible to separate (Z)-1-chloro-3,3,3-trifluoropropene by distillation.

In the present invention, it is preferable that the extractant is of the type capable of changing the relative volatility to be higher than 1 in order to flow (Z)-1-chloro-3,3,3-trifluoropropene out of the reaction system in view of material handling during production. It is also preferable that the extractant is of the type having a sufficiently high boiling point in order that the extractant can be easily separated from the distillate, that is, 1-chloro-1,3,3,3-tetrafluoropropane.

Further, it is preferable that the extractant is a material or intermediate product that, even when added into the reaction system, exerts no effect on the reaction system. For the industrial application, it is preferable that the extractant is of the type readily available at low cost. The extractant suitably compliant with these conditions is at least one kind of compound selected from the group consisting of halogenated hydrocarbons of the formula [2], halogenated unsaturated hydrocarbons, nitriles, ketones, carbonates, ethers, esters and alcohols.

Various volatility-changeable materials including the above extractant compounds are indicated in TABLE 1.

TABLE 1

| Extract | Relative volatility ($\alpha$) |
| --- | --- |
| None | 1.1 |
| 1,1-Dicloro-3,3,3-triluforopropane | 1.5 |
| 1,1,3-Trichloro-3,3-difluoropropane | 1.3 |
| 1,1,1,3,3-Pentafluoropropane | 1.2 |
| 1,1,2-Trichloro-3,3,3-trifluoropropane | 1.4 |
| 1,2-Dichloro-3,3,3-trifluoropropane | 1.3 |
| Acetonitrile | 2.3 |
| Ethanol | 0.4 |
| 2,2,3,3-Tetrafluoropropanol | 1.5 |
| 1-Trifluoromethyl-2,2,2-trifluoroethanol | 1.9 |
| Heptafluorocyclopentane (Zeorora H) | 1.4 |
| Acetone | 3.3 |
| N-methylpyrrolidone | 1.3 |
| Dimethyl sulfoxide | 1.4 |
| Dimethylformamide | 1.3 |
| Methyl ethyl ketone | 1.4 |
| Dimethyl carbonate | 2.1 |
| Triethyl orthoformate | 1.4 |
| 1,3-Dioxolane | 2.2 |
| Dimethyl sulfate | 1.5 |
| 1,4-Dioxane | 1.8 |
| Acetylacetone | 1.4 |
| $\gamma$-Butyrolactone | 1.5 |

Relative volatility measurement method: add 100 g of the extractant to the mixture of 40 g of (Z)-1-chloro-3,3,3-trifluoropropene (A) and 10 g of 1-chloro-1,3,3,3-tetrafluoropropane (B) and measure the resulting liquid or gas phase composition by gas chromatography Specific examples of the halogenated hydrocarbons are 1,1-dichloro-3,3,3-trifluoropropane, 1,1,3-trichloro-3,3-difluoropropane, 1,1,2-trichloro-3,3,3-trifluoropropane and 1,1,1,3,3-pentachloropropane. Among others, 1,1-dichloro-3,3,3-trifluoropropane is preferred. Specific examples of the halogenated unsaturated hydrocarbons are 1,2-dichloro-3,3,3-trifluoropropene, 1,2,3-trichloro-3,3-difluoropropene, 1,2,3,3-tetrachloro-3-fluoropropene, 1,3-dichloro-3,3-difluoropropene, 2,3-dichloro-3,3-difluoropropene, 1,3,3-trichloro-3-fluoropropene and 2,3,3-trichloro-3-fluoropropene. Specific examples of the ketones are acetone, methyl ethyl ketone and cyclohexanone. Among others, acetone is preferred. Specific examples of the nitriles are acetonitrile, propionitrile and butyronitrile. Among others, acetonitrile is preferred. Specific examples of the carbonates are dimethyl carbonate, diethyl carbonate, dipropyl carbonate and dibutyl carbonate. Among others, dimethyl carbonate is preferred. Specific examples of the ethers are dipropyl ether, dibutyl ether, tetrahydrofuran, 1-3-dioxolane and 1,4-dioxane. Among others, preferred are 1,3-dioxolane and 1,4-dioxane. Specific examples of the esters are methyl acetate, ethyl acetate, propyl acetate, butyl acetate, triethyl orthoformate, dimethyl sulfate and $\gamma$-butyrolactone. Specific examples of the alcohols are methanol, ethanol, isopropanol, buthanol, 2,2,3,3-tetrafluoropropanol and 1-trifluoromethyl-2,2,2-trifluoroethanol. There can also be used sulfoxides such as dimethyl sulfoxide, amides such as dimethylformamide and pyrrolidones such as N-methylpyrrolidone. These compounds can be used solely or in the form of a mixture of two or more thereof.

When the extractant compound is soluble in water, a mixture of such a water-soluble extractant compound and water may be used as the extractant. For example, it is feasible to use an aqueous solution of acetone, acetonitrile, dioxane or $\gamma$-lactone as the extractant. In this case, the mixing ratio of the organic extractant compound and water is set in such a manner that the amount of water in the solution is less than 50 mass % in view of extraction efficiency.

The extractant may be used as a mixed system with water by separately adding water to the water-soluble extractant compound when the water-soluble compound is used as the extractant. The mixed system of the extractant and water can be adjusted as appropriate by any skilled in the art.

When the water-soluble compound is used as the extractant, the extractant may coexist with the target compound, (Z)-1-chloro-3,3,3-trifluoropropene in the distillate. In such a case, the target compound can be easily separated from the extractant by washing with water etc.

The extractant has a normal boiling point different in temperature, generally by 20° C. or more, from that of the target compound of the present invention so as to allow separation of the extractant and the target compound of the present invention by simple distillation, stripping etc. The normal boiling point of the extractant is favorably in the range of 50 to 220° C., preferably 60 to 120° C.

In the present invention, there may be used the extractant whose normal boiling point exceeds 220° C. When the boiling point of the extractant is extremely high, however, the amount of heat energy for recovery of the extractant becomes large. This leads to increase in the economical load. It is thus preferable that the boiling point of the extractant used is within the above range. When the boiling point of the extractant is lower than 50° C., the extractive distillation may not provide a satisfactory separation effect. It is thus not so favorable to use such a low boiling point extractant.

There is no particular limitation on the amount of the extractant used in the method of the present invention. In general, the efficiency of extractive separation of the target compound increases with the ratio of the amount extractant to that of the raw material (i.e. the extractant concentration). It is economically unfavorable that the extractant amount ratio is too high in view of equipment upsizing and utility increase. It is also economically unfavorable that the extractant amount ratio is too low as the separation effect of the extractive distillation is so little that the product purity cannot be made high. The amount of the extractant is generally preferably in the range of 10 to 10000 parts by mass, more preferably 50 to 5000 parts by mass, still more preferably 100 to 200 parts by mass, per 100 parts by mass of the raw material.

The method of the present invention can be performed with the use of a distillation column. Preferably, the distillation column is a packed column or a plate column. In order to distribute the extractant throughout the distillation column, a plate of the distillation column to which the extractant is introduced is located nearer to the top of the column than a plate of the distillation column to which the raw material is fed. The number of plates between the plate to which the extractant is introduced and the plate to which the raw material is fed, the number of plates between the plate to which the extractant is introduced and the top of the column, the number of plates between the plate to which the raw material is fed and the bottom of the column can be selected as appropriate in preliminary consideration of the relationship between the purity and recovery rate of the distillate.

When the extractant is capable of changing the relative volatility to be higher than 1, the extractive distillation is conducted by distilling (Z)-1-chloro-3,3,3-trifluoropropene from the top of the column and recovering the extractant and 1-chloro-1,3,3,3-tetrafluoropropane in a distillation still. There is also no particular limitation on the distillation operation conditions such as the temperatures of the respective areas in the distillation column, the plate to which the raw material is fed and the amount of the extractant introduced. These operation conditions depend on the performance of the distillation column, the content ratio of (Z)-1-chloro-3,3,3-trifluoropropene and 1-chloro-1,3,3,3-tetrafluoropropane in the material to be treated (i.e. the raw material), the kind and amount of the extractant used and the like and can be set by preliminary experiment. Further, the extractant may be added to the raw material so as to maintain stable distillation operation. Although the method of the present invention can be performed by discontinuous process or continuous process, it is industrially preferable to perform the method of the present invention by continuous process. It is possible to increase the purity of the distillate by repeated cycles of extractive distillation operations.

The mixture of the extracted fraction of the raw material and the extractant can be separated by stripping, distillation etc. so as to return the separated fraction of the raw material to the reaction system and to recycle and reuse the extractant for extractive distillation operation. Namely, it is feasible to distill the mixture containing the extractant and either 1-chloro-1,3,3,3-tetrafluoropropane or (Z)-1-chloro-3,3,3-trifluoropropene extracted with the extractant, thereby separating the extractant and either 1-chloro-1,3,3,3-tetrafluoropropane or (Z)-1-chloro-3,3,3-trifluoropropene from the mixture, return the separated 1-chloro-1,3,3,3-tetrafluoropropane or (Z)-1-chloro-3,3,3-trifluoropropene to the reaction system and recover and recycle the separated extractant. This is a preferred embodiment of the present invention for significant reduction in waste.

In the method of the present invention, there can be used a reaction vessel of glass, a reaction vessel of stainless steel or a reaction vessel of carbon steel with a lining of tetrafluoroethylene resin, chlorotrifluoroethylene resin, vinylidene fluoride resin, PFA resin or the like.

The present invention will be described in more detail below by way of the following examples. It is noted that the following examples are illustrative and are not intended to limit the present invention thereto. In the following examples, percentages "%" are by mass.

EXAMPLES

Herein, a mixture of (Z)-1-chloro-3,3,3-trifluoropropene, (E)-1-chloro-3,3,3-trifluoropropene and 1-chloro-1,3,3,3-tetrafluoropropane was obtained by a conventional, known process and subjected to distillation, thereby separating (E)-1-chloro-3,3,3-trifluoropropene. The resulting mixture of (Z)-1-chloro-3,3,3-trifluoropropene and 1-chloro-1,3,3,3-tetrafluoropropane was used as a starting material in the following examples and comparative example.

Example 1

A glass rectification column of 26 mm in column diameter, equipped with a vacuum jacket and having a theoretical plate number of 50, was packed with a stainless steel packing material (Heli Pack No. 2 manufactured by Tokyo Tokusyu Kanaami Co., Ltd.). A raw material containing 83.6% (Z)-1-chloro-3,3,3-trifluoropropene and 16.4% 1-chloro-1,3,3,3-tetrafluoropropane was fed into the rectification column at 81.0 g/h from through an inlet portion at the 40th plate from the top of the column, whereas 1,1-dichloro-3,3,3-trifluoropropane was fed into the rectification column at 801.0 g/h from through an inlet portion at the 10th plate from the top of the column. In this state, distillation of the raw material was performed under ordinary pressure at a reflux ratio of 5 and a bottom temperature of 70° C. A distillate was obtained at 68.1 g/h from the top of the column; and a bottom product was obtained at 813.9 g/h. The compositions of the raw material, distillate and bottom product are indicated in TABLE 2.

TABLE 2

|  |  | Raw material | Extractant | Distillate | Bottom product |
|---|---|---|---|---|---|
| Flow rate (g/h) |  | 81.0 | 801.0 | 68.1 | 813.9 |
| Composition | 1233Z | 83.6 | — | 98.0 | 0.1 |
| % | 244fa | 16.4 | — | 2.0 | 1.5 |
|  | 243fa | — | 99.9 | — | 98.4 |

1233Z: (Z)-1-chloro-3,3,3-trifluoropropene
244fa: 1-chloro-1,3,3,3-tetrafluoropropane
243fa: 1,1-dichloro-3,3,3-trifluoropropane Example 2

A glass rectification column of 26 mm in column diameter, equipped with a vacuum jacket and having a theoretical plate number of 33, was packed with a stainless steel packing material (Dixon Packing manufactured by Tokyo Tokusyu Kanaami Co., Ltd.). A raw material containing 82.6% (Z)-1-chloro-3,3,3-trifluoropropene and 17.4% 1-chloro-1,3,3,3-tetrafluoropropane was fed into the rectification column at 22.8 g/h from through an inlet portion at the 28th plate from the top of the column, whereas dimethyl carbonate was fed into the rectification column at 197.2 g/h from through an inlet portion the 10th plate from the top of the column. In this state, distillation of the raw material was performed under ordinary pressure at a reflux ratio of 5 and a bottom temperature of 91° C. A distillate was obtained at 18.5 g/h from the top of the column; and a bottom product was obtained at 201.5 g/h. The compositions of the raw material, distillate and bottom product are indicated in TABLE 3.

TABLE 3

|  |  | Raw material | Extractant | Distillate | Bottom product |
|---|---|---|---|---|---|
| Flow rate (g/h) |  | 22.8 | 197.2 | 18.5 | 201.5 |
| Composition | 1233Z | 82.6 | — | 99.6 | 0.2 |
| % | 244fa | 17.4 | — | 0.4 | 1.9 |
|  | DMC | — | 99.9 | — | 97.9 |

1233Z: (Z)-1-chloro-3,3,3-trifluoropropene
244fa: 1-chloro-1,3,3,3-tetrafluoropropane
DMC: dimethyl carbonate Example 3

A glass rectification column of 26 mm in column diameter, equipped with a vacuum jacket and having a theoretical plate number of 50, was packed with a stainless steel packing material (Heli Pack No. 2 manufactured by Tokyo Tokusyu Kanaami Co., Ltd.). A raw material containing 82.6% (Z)-1- chloro-3,3,3-trifluoropropene and 17.4% 1-chloro-1,3,3,3-tetrafluoropropane was fed into the rectification column at 81.0 g/h from through an inlet portion at the 40th plate from the top of the column, whereas acetonitrile was fed into the rectification column at 797.9 g/h from through an inlet portion at the 10th plate from the top of the column. In this state, distillation of the raw material was performed under ordinary pressure at a reflux ratio of 5 and a bottom temperature of 82° C. A distillate was obtained at 64.1 g/h from the top of the column; and a bottom product was obtained at 814.8 g/h. The compositions of the raw material, distillate and bottom product are indicated in TABLE 4.

TABLE 4

|  |  | Raw material | Extractant | Distillate | Bottom product |
|---|---|---|---|---|---|
| Flow rate (g/h) |  | 81.0 | 797.9 | 64.1 | 814.8 |
| Composition | 1233Z | 82.6 | — | 99.0 | 0.4 |
| % | 244fa | 17.4 | — | 1.0 | 1.7 |
|  | acetonitrile | — | 99.9 | — | 97.9 |

1233Z: (Z)-1-chloro-3,3,3-trifluoropropene
244fa: 1-chloro-1,3,3,3-tetrafluoropropane Example 4

A glass rectification column of 26 mm in column diameter, equipped with a vacuum jacket and having a theoretical plate number of 50, was packed with a stainless steel packing material (Heli Pack No. 2 manufactured by Tokyo Tokusyu Kanaami Co., Ltd.). A raw material containing 82.6% (Z)-1-chloro-3,3,3-trifluoropropene and 17.4% 1-chloro-1,3,3,3-tetrafluoropropane was fed into the rectification column at 81.0 g/h from through an inlet portion at the 40th plate from the top of the column, whereas acetone was fed into the rectification column at 793.8 g/h from through an inlet portion at the 10th plate from the top of the column. In this state, distillation of the raw material was performed under ordinary pressure at a reflux ratio of 5 and a bottom temperature of 57° C. A distillate was obtained at 228.4 g/h from the top of the column; and a bottom product was obtained at 646.4 g/h. The compositions of the raw material, distillate and bottom product are indicated in TABLE 5.

TABLE 5

|  |  | Raw material | Extractant | Distillate | Bottom product |
|---|---|---|---|---|---|
| Flow rate (g/h) |  | 81.0 | 793.8 | 228.4 | 646.4 |
| Composition | 1233Z | 82.6 | — | 14.7 | 5.2 |
| % | 244fa | 17.4 | — | — | 2.2 |
|  | acetone | — | 99.9 | 85.3 | 92.6 |

1233Z: (Z)-1-chloro-3,3,3-trifluoropropene
244fa: 1-chloro-1,3,3,3-tetrafluoropropane Example 5

A glass rectification column of 26 mm in column diameter, equipped with a vacuum jacket and having a theoretical plate number of 50, was packed with a stainless steel packing material (Heli Pack No. 2 manufactured by Tokyo Tokusyu Kanaami Co., Ltd.). A raw material containing 82.6% (Z)-1-chloro-3,3,3-trifluoropropene and 17.4% 1-chloro-1,3,3,3-tetrafluoropropane was fed into the rectification column at 40.5 g/h from through an inlet portion at the 40th plate from the top of the column, whereas a mixed solvent of acetone/water ($H_2O$) weight ratio=90/10 was fed into the rectification column at 324.4 g/h from through an inlet portion at the 10th plate from the top of the column. In this state, distillation of the raw material was performed under ordinary pressure at a reflux ratio of 5 and a bottom temperature of 58° C. A distillate was obtained at 70.9 g/h from the top of the column; and a bottom product was obtained at 294.0 g/h. The compositions of the raw material, distillate and bottom product are indicated in TABLE 6.

TABLE 6

|  |  | Raw material | Extractant | Distillate | Bottom product |
|---|---|---|---|---|---|
| Flow rate (g/h) |  | 40.5 | 324.4 | 70.9 | 294.0 |
| Composition | 1233Z | 82.6 | — | 24.1 | 5.6 |
| % | 244fa | 17.4 | — | 0.1 | 2.4 |
|  | acetone | — | 90.0 | 74.7 | 81.3 |
|  | water | — | 10.0 | 1.1 | 10.7 |

1233Z: (Z)-1-chloro-3,3,3-trifluoropropene
244fa: 1-chloro-1,3,3,3-tetrafluoropropane Comparative Example 1

A glass rectification column of 26 mm in column diameter, equipped with a vacuum jacket and having a theoretical plate number of 50, was packed with a stainless steel packing material (Heli Pack No. 2 manufactured by Tokyo Tokusyu Kanaami Co., Ltd.). A raw material containing 83.8% (Z)-1-chloro-3,3,3-trifluoropropene and 16.2% 1-chloro-1,3,3,3-tetrafluoropropane was fed into the rectification column at 130.0 g/h from through an inlet portion at the 42th plate from the top of the column. In this state, distillation of the raw material was performed under ordinary pressure at a reflux ratio of 5 and a bottom temperature of 39° C. A distillate was obtained at 58.3 g/h from the top of the column; and a bottom product was obtained at 71.7 g/h. The compositions of the raw material, distillate and bottom product are indicated in TABLE 7.

TABLE 7

|  |  | Raw material | Distillate | Bottom product |
|---|---|---|---|---|
| Flow rate (g/h) |  | 130.0 | 58.3 | 71.7 |
| Composition | 1233Z | 83.8 | 89.1 | 79.4 |
| % | 244fa | 16.2 | 10.9 | 20.6 |

1233Z: (Z)-1-chloro-3,3,3-trifluoropropene
244fa: 1-chloro-1,3,3,3-tetrafluoropropane

The invention claimed is:
1. A method of purifying (Z)-1-chloro-3,3,3-trifluoropropene of the formula [1], comprising: distilling a mixture containing (Z)-1-chloro-3,3,3-trifluoropropene of the formula [1] and 1-chloro-1,3,3,3-tetrafluoropropane ($CF_3CH_2CHClF$),

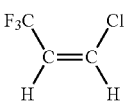

[1]

wherein the distilling is performed by extractive distillation of the mixture in the coexistence of at least one kind of compound selected from the group consisting of halogenated hydrocarbons of the formula [2], halogenated unsaturated hydrocarbons, nitriles, ketones, carbonates, ethers, esters and alcohols as an extractant in a reaction system $$CF_nCl_{3-n}CHXCClF_mH_{2-m} \quad [2]$$

where X represents a hydrogen atom (H), a fluorine atom (F) or a chlorine atom (Cl); n represents an integer of 0 to 3; and m represents an integer of 0 to 2.

2. The method according to claim 1, wherein the halogenated hydrocarbons are at least one selected from the group consisting of 1,1-dichloro-3,3,3-trifluoropropane, 1,1,3-trichloro-3,3-difluoropropane, 1,1,1,3,3-pentachloropropane and 1,1,2-trichloro-3,3,3-trifluoropropane.

3. The method according to claim 1, wherein the halogenated unsaturated hydrocarbons are at least one selected from the group consisting of 1,2-dichloro-3,3,3-trifluoropropene, 1,2,3-trichloro-3,3-difluoropropene, 1,2,3,3-tetrachloro-3-fluoropropene, 1,3-dichloro-3,3-difluoropropene, 2,3-dichloro-3,3-difluoropropene, 1,3,3-trichloro-3-fluoropropene and 2,3,3-trichloro-3-fluoropropene.

4. The method according to claim 1, wherein the extractant comprises at least one compound selected from the group consisting of 1,1-dichloro-3,3,3-trifluoropropane, 1,1,3-trichloro-3,3-difluoropropane, 1,1,1,3,3-pentachloropropane, 1,1,2-trichloro-3,3,3-trifluoropropane, acetone, acetone/water, acetonitrile, dimethyl carbonate, ethanol, 1-trifluoromethyl-2,2,2-trifluoroethanol, 1,3-dioxolane, 1,4-dioxane and γ-butyrolactone.

5. The method according to claim 1, wherein the extractant has a normal boiling point of 50 to 220° C.

6. The method according to claim 1, wherein the extractant contains less than 50 mass % of water.

7. The method according to claim 1, wherein the amount of the extractant is 10 to 10000 parts by weight per 100 parts by mass of the mixture containing the 1-chloro-3,3,3-trifluoropropene of the formula [1] and the 1-chloro-1,3,3,3-tetrafluoropropane.

8. The method according to claim 1, further comprising:
distilling a mixture obtained after the extractive distillation and containing the extractant and either the 1-chloro-1,3,3,3-tetrafluoropropane or (Z)-1-chloro-3,3,3-trifluoropropene extracted with the extractant, thereby separating the extractant and the 1-chloro-1,3,3,3-tetrafluoropropane or (Z)-1-chloro-3,3,3-trifluoropropene from the mixture;
returning the separated 1-chloro-1,3,3,3-tetrafluoropropane or (Z)-1-chloro-3,3,3-trifluoropropene to the reaction system; and
recovering and reusing the separated extractant.

* * * * *